United States Patent [19]

Kuhrts

[11] Patent Number: 4,911,917

[45] Date of Patent: Mar. 27, 1990

[54] CHOLESTEROL-LOWERING COMBINATION COMOPSITIONS OF MAGNESIUM SALT AND NIACIN

[75] Inventor: Eric H. Kuhrts, Santa Barbara, Calif.

[73] Assignee: Hauser-Kuhrts, Inc., Santa Barbara, Calif.

[21] Appl. No.: 212,607

[22] Filed: Jun. 28, 1988

[51] Int. Cl.⁴ .................... A61K 33/06; A61K 31/44
[52] U.S. Cl. ..................................... 424/10; 424/682; 514/356
[58] Field of Search .................. 424/10, 154; 514/356

[56] References Cited

PUBLICATIONS

Chemical Abstracts 106(4):23311y, Stronheim, 1/26/87.
Chemical Abstracts, 84(3):17156, Schlager, 1/19/76.

Primary Examiner—Douglas W. Robinson
Assistant Examiner—Raymond J. Henley, III
Attorney, Agent, or Firm—Gordon W. Hueschen

[57] ABSTRACT

An antihyperlipidemic pharmaceutical or dietary supplement composition for oral use consisting essentially of a combination of niacin and a physiologically-acceptable magnesium salt, and a method of lowering cholesterol levels with such oral pharmaceutical composition, or by the simultaneous oral administration of the active ingredients thereof, which eliminates the usual undesirable flushing side effect of niacin, is disclosed.

20 Claims, No Drawings

CHOLESTEROL-LOWERING COMBINATION COMOPSITIONS OF MAGNESIUM SALT AND NIACIN

BACKGROUND OF THE INVENTION

1. Field of Invention

Antihyperlipidemic pharmaceutical or dietary supplement compositions and method of treating hyperlipidemic conditions therewith; combination compositions and therapy employing niacin and a magnesium salt which ameliorates or substantially reduces the usual undesirable side effects of niacin.

2. Background of the Invention and Prior Art

Nicotinic acid was the only agent studied by the *Coronary Drug Project* which produced a significant decrease in coronary events. Coronary Drug Project Research Group: Clofibrate and Niacin and Coronary Heart Disease. JAMA 231:360 (1975). This research demonstrated that niacin lowers blood cholesterol on an average by nine percent and reduces the recurrence rate of myocardial infarction by 29%. The study involved more than 8,000 individuals and was conducted over a period of six (6) years. The usual dosage range for niacin therapy is 3 to 6 grams per day, which dosage is capable of lowering cholesterol level from 10 to 25%, triglyceride level by 45 to 50%, and elevating HDL cholesterol by 15 to 20%.

In a paper in the Journal of Lipid Research 22:24–36 (1981) entitled "Influence of Nicotinic Acid on Metabolism of Cholesterol and Triglycerides in Man", it is stated as follows:

"Although the magnitude of plasma lipid lowering by nicotinic acid can be appreciable, its usefulness has been limited by certain disagreeable side effects such as flushing of the face and other skin reactions."

Although the actual mechanisms by which niacin reduces cholesterol and triglycerides is not completely known, it is known that niacin does produce these effects and that niacin, moreover, has an ability to increase the amount of the protective form of cholesterol, namely, HDL cholesterol.

A major shortcoming of niacin is the necessity of administering large doses of niacin to effectively lower cholesterol level. Most subjects treated will experience accompanying side effects of flushing, prickling of the skin, and itching when they begin niacin, when the dosage is increased, or when the treatment is temporarily terminated and then commenced once more at the same dose. Ordinarily, it is necessary for a subject to gradually increase the dosage of niacin to a three to six gram per day dosage level over a period of months, starting with one 50 mg tablet three times daily for a total dose of 150 mg per day, to avoid being overwhelmed with the unpleasant side effects.

The prior art is replete with reports of the reduction of cholesterol levels and control of cholesterol levels in a subject in need of the same employing niacin (nicotinic acid) and of the undesirable side effects ordinarily produced when an effective amount of niacin is employed for such purpose. The side effects include flushing and itching, and it is well documented in the literature that such flushing, itching, and so on is not eliminated by intermittent niacin therapy, and generally reappears even when the therapy is interrupted and reinstituted. Although the degree or intensity of such side effects varies from patient to patient, it is frequently observed that such therapy cannot be applied in the case of various patients who are hypersensitive to the niacin or to the side effects which result in such patients upon oral administration thereof.

Numerous other approaches to the lowering of cholesterol in a subject in need thereof have been proposed. For example, cholestyramine and other drugs which theoretically affect the bile acid pool and pull cholesterol out of the bloodstream according to the postulated mechanism are also available as are the dietary fiber materials, such as guar gum and the like. Guar gum has been suggested as a dietary supplement fiber having an effect on cholesterol upon ingestion, but having a somewhat reduced effect when compared to bile acid-binding agents such as cholestyramine.

Dietary supplements or regimens combining oat bran and niacin have been recommended, but there has been no evidence or suggestion that such combination dietary treatment or approach has any effect upon the undesirable side effects of niacin, least of all at cholesterol-lowering dosages or intakes. Accordingly, its side effects continue to hamper its general applicability in cholesterol lowering and poor patient compliance often results because of these side effects.

It is accordingly reported that "Continuous flushing, resulting from harmless dilation of skin capillaries, occurs in most individuals at onset of treatment and when dosage is increased.--- Patients should be warned that if several doses are missed, the flushing will recur.--- Gastric irritation is also frequently encountered.---"

Since niacin is very effective in reduction of undesirable cholesterol levels, which reportedly fall by a mean of approximately 22% during some controlled clinical evaluations, it would be highly desirable to provide a way in which this valuable cholesterol-lowering material could be more generally applied without fear of or limitation by the said undesirable side effects, and the present invention addresses this problem, which has heretofore had no satisfactory solution, by combined therapy employing also a magnesium salt which is soluble in the gastric juices, and which unpredictably, as found according to the present invention, at least very substantially reduces the usual niacin side effects when administered simultaneously and preferably in a combination composition therewith.

Combination therapy employing colestipol, a bile acid sequestrant, together with niacin or its prodrug clofibrate, produced reduction in cholesterol levels as expected, which were greater when niacin was used together with colestipol rather than its prodrug clofibrate, but care still had to be taken to "mitigate the prostaglandin-mediated cutaneous flushing often associated with niacin", aspirin therefore being administered a half hour before each dose of niacin for this purpose. Combination therapy involving Lovastatin, plus a resin such as cholestyramine or colestipol, and niacin has also been suggested, it being reported that the Lovastatin reduced the amount of resin and niacin required to produce satisfactory results, and providing a possible powerful therapy for severe familial hypercholesterolemia, although such bile acid-sequestering resins are suspect as possibly binding and at least partially inactiviting niacin as well. In any case, the combination of niacin plus a magnesium salt, as provided by the present invention, would appear to be a much simpler solution to the problem of the undesirable niacin side effects, at the same time providing effective cholesterol-lowering effect and results, than any combination, method-oftreating, or dietary supplement approach which has been suggested previously. Up to the time of this invention, no one has disclosed or even suggested that a combination of a magnesium salt and niacin could greatly reduce the unpleasant and normally limiting side effects of niacin in addition to providing efficient cholesterol-lowering effect.

A Dialog search from the U.S. Patents data base for niacin for U.S. Patent Abstracts 97-81, 1982-1987, and weekly from 12/87 through the middle of February 1988, turned up a few niacin prodrugs with or without allegedly reduced side effects and U.S. Pat. No. 4,166,902 relating to high polymers containing nicotinic acid in which nicotinic acid radicals are bound through covalent ester bonds which gradually hydrolyze in a biological environment by setting free nicotinic acid, and which allegedly have a therapeutic activity similar to that of nicotinic acid itself but longer lasting and with the elimination or least reduction of "collateral effects", the product of this patent apparently being some sort of a "depo" nicotinic acid-containing material, but of course the question remains whether the slow release of nicotinic acid as disclosed in this patent will provide adequate niacin levels for effective cholesterol lowering in practice. At any rate, this patent merely emphasizes the continued existence of the problem of niacin side effects and allegedly provides one approach to its possible solution, being in no way suggestive of the entirely different solution to the problem discovered by the present applicant.

OBJECTS OF THE INVENTION

It is an object of the present invention to provide a method of lowering cholesterol, especially LDL cholesterol, in a subject in need of the same, by the employment of nicotinic acid (niacin) in combination with a magnesium salt, especially magnesium carbonate or oxide, which is highly effective for its intended purpose and which has the further advantageous and unpredictable effect of substantially reducing the usual flushing and related side effects of niacin. A further object of the invention is the provision of such a method wherein the niacin and the magnesium salt are administered simultaneously. An additional object of the invention is the provision of a combination composition comprising both niacin and a magnesium salt which is useful for the aforesaid purpose. Still a further object of the present invention is the provision of such a method and such a combination composition which may be employed in the reduction of cholesterol levels either as or as a part of a medical or a pharmaceutical regimen or therapy for the reduction of cholesterol levels in a subject in need of the same, or as a food supplement for the effective reduction of cholesterol levels in a subject in need of the same according to good-health dietary practices for or by a subject desiring to reduce cholesterol levels to or maintain the same at levels which are considered to be acceptable and/or relatively safe from a dietary or medical standpoint. Further objects of the invention will become apparent hereinafter, and still others will be obvious to one skilled in the art to which this invention pertains.

SUMMARY

In summary then, the present invention comprises, inter alia, the following, singly or in combination:

An oral antihyperlipidemic composition of nicotinic acid characterized by reduced flushing effect comprising as active ingredients nicotinic acid and an amount of a physiologically-acceptable magnesium salt effective for said purpose; such a composition wherein the composition contains at least about 50 mg of nicotinic acid; such a composition wherein the amount of nicotinic acid is at least about 50 mg and the amount of magnesium salt is at least about 50 mg; such a composition wherein the amount of nicotinic acid is at least about 50 mg and the amount of magnesium salt is at least about 200 mg, in capsule or tablet form; and such a composition comprising about 50-200 mg niacin and about 50-500 mg magnesium carbonate or oxide. Moreover, a method of combating hyperlipidemia in a subject in need of the same using nicotinic acid characterized by reduced flushing effect comprising the step of simultaneously administering orally to the said subject both nicotinic acid and an amount of a physiologically-acceptable magnesium salt effective for said purpose; such a method comprising the step of administering orally to the said subject both nicotinic acid and a physiologically-acceptable magnesium salt in the form of a pharmaceutical composition containing both ingredients; such a method comprising the step of administering orally to the said subject both nicotinic acid and a physiologically-acceptable magnesium salt in the form of a pharmaceutical composition containing both ingredients in capsule or tablet form; such a method wherein a single dosage comprises at least about 150 mg of niacin and at least about 150 mg of a physiologically-acceptable magnesium salt; such a method wherein a single dosage comprises about 200-400 mg niacin and about 400-800 mg of a physiologically-acceptable magnesium salt; such a method wherein a dosage unit comprises at least about 50 mg magnesium salt and at least about 50 mg niacin; such a method wherein a single dosage comprises at least about 500 mg of magnesium salt and at least about 200 mg of niacin; such a method wherein a daily dose comprises at least about 600 mg niacin and at least about 1.5 g magnesium carbonate; and such a method wherein the magnesium salt is magnesium carbonate or oxide.

GENERAL DESCRIPTION OF THE INVENTION

The invention, in general, is set forth under "Objects of the Invention" and "Summary of the Invention" but, in short, comprises the combination with niacin of a magnesium salt which is soluble in the gastric juices, e.g., the carbonate, hydroxide, oxide, chloride, or the like, with the resulting effect that an extremely effective oral antihypercholesterolemic combination is provided, preferably in a single-dosage unit form. Alternatively, the two ingredients may be orally administered simultaneously, although administration of both together in a combination composition is preferred. In addition to the desired antihypercholesterolemic effect of the combination and combination therapy of the present invention, the usual cutaneous flushing, resulting in itching or prickling of the skin, as well as bright-red blushing, which ordinarily results from harmless dilation of the skin capillaries in the course of niacin therapy and which frequently manifests itself even at a niacin dose as low as 50 mg, has unpredictably been found to be greatly reduced or essentially eliminated when the niacin is administered or ingested in combination with the magnesium salt. The exact form in which the active ingredients are orally administered is not important, so long as the objectives of the invention are obtained. The active ingredients may take the form of the usual tablets, capsules, suspensions, dispersions, elixirs, syrups, or the like, whether administered singly or in combination, and may moreover be provided in the usual form for dietary supplements involving inclusion in capsules, drink mixes, breakfast foods, or the like.

DETAILED DESCRIPTION OF THE INVENTION

The following Examples are given to illustrate the invention, but are not to be construed as limiting.

EXAMPLE 1

A composition is prepared according to the following formula:

Magnesium salt (oxide) 50-250 mg
Niacin (nicotinic acid) 50-100 mg

These ingredients, the magnesium salt and niacin, are blended together and encapsulated in a hard gelatine capsule or formulated into a tablet. A lubricating agent may as usual be used to facilitate encapsulation. This formula can be orally ingested at an effective therapeutic dose of two (2) capsules or tablets, preferably three (3) times a day.

At a dosage of two (2) capsules, the amount of active ingredients is 100-500 mg of magnesium (as salt) and 100-200 mg of niacin.

When this dosage is taken three (3) times daily, the total amount of magnesium (as oxide) is 150-1500 mg and the amount of niacin is 300-600 mg.

EXAMPLE 2

The amounts of niacin and magnesium (as the oxide) in the composition of this Example are 250 mg and 100 mg, respectively, per tablet. At a dose of two (2) capsules, this makes the amount of magnesium oxide 500 mg and the amount of niacin 200 mg and, at a TID regimen, the number of capsules 6 per day, the amount of magnesium oxide ingested then being 1.5 grams and the amount of niacin 600 mg.

EXAMPLE 3

In additional formulations, magnesium chloride, magnesium hydroxide, or other physiologically-acceptable magnesium salt is employed in place of the magnesium oxide, with substantially identical results.

PHARMACOLOGICAL AND CLINICAL EVALUATION

A. The properties of the combination composition of Example 1 are examined clinically, at a dosage of two (2) capsules TID, making 6 per day in all, taken at mealtime, over a period of two (2) weeks. The five (5) subjects in the test panel normally experienced niacin side effects at a 50 mg initial dose.

The formulation of the invention, at the level employed, greatly reduced the side effects of niacin, such as cutaneous flushing, resulting in itching or prickling of the skin and bright-red blushing, as previously experienced by the members of the test panel.

B. In similar clinical tests conducted using the formulation set forth in Example 2, the results are essentially identical.

C. The formulations of Example 3 produce results equivalent to those set forth under "A" from the standpoint of reduced side effects of the niacin.

Alternatively, these results can be observed by administering the active ingredients nicotinic acid and magnesium salt simultaneously. As already pointed out, another physiologically-acceptable magnesium salt which is soluble in the gastric fluids can be substituted for the magnesium oxide and carbonate of the Examples.

According to the practice of the art, the niacin or nicotinic acid may be provided as such or in the form of a prodrug thereof, numerous of which are presently available and which break down, to a greater or lesser extent upon ingestion, to provide nicotinic acid in the system of the subject orally ingesting the same for reduction or control of cholesterol levels in the said subject. Representative prodrugs of this type are derivatives of nicotinic acid, especially esters, amides, and the like, and many of these prodrugs are also subject to the same side effects as niacin itself, namely, the production of the undesirable and sometimes intolerable side effects of flushing, itching, and the like and, to the extent that these prodrugs do provide nicotinic acid upon ingestion, as well as the undesirable side effects of niacin previously mentioned, they may be employed according to the present invention in lieu of niacin itself, the method and combination compositions of the present invention providing effective cholesterol-lowering effect as well as reduction or essential elimination of the undesirable effects of niacin when such a prodrug is employed just as in the case of the employment of niacin itself.

It is therefore seen that the present invention provides an oral antihyperlipidemic composition of nicotinic acid (niacin) characterized by reduced and related flushing effects comprising as active ingredients nicotinic acid and a physiologically-acceptable magnesium salt, whether organic or inorganic in nature, which is effective in lowering of cholesterol levels, without the usual undesirable flushing and related side effects of niacin, and a method of lowering cholesterol levels by employment of such an oral pharmaceutical or dietary supplement composition, or by the simultaneous oral administration of the ingredients thereof, all having the unpredictable and highly advantageous characteristics and effects as more fully set forth in the foregoing.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

I claim:

1. An oral antihyperlipidemic composition of nicotinic acid, having a reduced flushing effect, consisting essentially of an effective antihyperlipidemic amount of nicotinic acid and an effective cutaneous-flushing-reducing amount of a physiologically-acceptable inorganic magnesium salt.

2. A composition of claim 1 wherein the composition contains at least about 50 mg of nicotinic acid.

3. A composition of claim 1 wherein the amount of nicotinic acid is at least about 50 mg and the amount of magnesium salt is at least about 50 mg.

4. A composition of claim 1 wherein the amount of nicotinic acid is at least about 50 mg and the amount of magnesium salt is at least about 200 mg, in capsule or tablet form.

5. A composition of claim 1 consisting essentially of about 50-200 mg nicotinic acid and
about 50-500 mg magnesium carbonate or oxide.

6. A method for reducing the cutaneous flushing caused by the administration of an effective antihyperlipidemic amount of nicotinic acid to a patient suffering from hyperlipidemia, consisting essentially of the step of simultaneously orally administering to said patient an effective cutaneous-flushing-reducing amount of a physiologically-acceptable magnesium salt and an effective antihyperlipidemic amount of nicotinic acid.

7. Method of claim 6 consisting essentially of the step of administering orally to the said patient both nicotinic acid and a physiologically-acceptable magnesium salt in the form of a pharmaceutical composition consisting essentially of both ingredients.

8. Method of claim 6 consisting essentially of the step of administering orally to the said patient both nicotinic acid and a physiologically-acceptable magnesium salt in the form of a pharmaceutical composition consisting essentially of both ingredients in capsule or tablet form.

9. Method of claim 6, wherein a single dosage consists essentially of at least about 150 mg of niacin and at least about 150 mg of a physiologically-acceptable magnesium salt.

10. Method of claim 6, wherein a single dosage consists essentially of about 200–400 mg niacin and about 400–800 mg of a physiologically-acceptable magnesium salt.

11. Method of claim 6 wherein a dosage unit consists essentially of at least about 50 mg magnesium salt and at least about 50 mg niacin.

12. Method of claim 6 wherein a single dose consists essentially of at least about 500 mg of magnesium salt and at least about 200 mg of niacin.

13. Method of claim 6 wherein a daily dose consists essentially of at least about 600 mg niacin and at least about 1.5 g magnesium carbonate.

14. Method of claim 6, wherein the magnesium salt is magnesium carbonate or oxide.

15. Method of claim 7, wherein a single dosage consists essentially of at least about 150 mg of niacin and at least about 150 mg of a physiologically-acceptable magnesium salt.

16. Method of claim 7, wherein a single dosage consists essentially of about 200–400 mg niacin and about 400–800 mg of a physiologically-acceptable magnesium salt.

17. Method of claim 7, wherein a dosage unit consists essentially of at least about 50 mg magnesium salt and at least about 50 mg niacin.

18. Method of claim 7, wherein a single dose consists essentially of at least about 500 mg of magnesium salt and at least about 200 mg of niacin.

19. Method of claim 7, wherein a daily dose consists essentially of a least about 600 mg niacin and at least about 1.5 g magnesium carbonate.

20. Method of claim 7, wherein the magnesium salt is magnesium carbonate or oxide.

* * * * *

UNITED STATES PATENT AND TRADEMARK OFFICE
CERTIFICATE OF CORRECTION

PATENT NO. : 4,911,917

DATED : March 27, 1990

INVENTOR(S) : Eric H. Kuhrts

It is certified that error appears in the above-identified patent and that said Letters Patent is hereby corrected as shown below:

Title Page, [54] line 2; "COMOPSITIONS" should read
  -- COMPOSITIONS --

Title Page, [56] References Cited; preceding "PUBLICATIONS"
  insert the following:    --        U.S. PATENT DOCUMENTS
                    4,166,902  9/1979  Ferruti   536/48 --

Title Page, [56] References Cited, PUBLICATIONS, line 2;
  ":17156," should read -- :17156n, --

Col. 3, line 9; "97-81" should read -- 1971-81 --

Col. 8, line 27; "a" should read -- at --

Signed and Sealed this

Twenty-first Day of May, 1991

Attest:

HARRY F. MANBECK, JR.

*Attesting Officer*   *Commissioner of Patents and Trademarks*